US00PP29218P3

(12) United States Plant Patent
Ranney

(10) Patent No.: US PP29,218 P3
(45) Date of Patent: Apr. 10, 2018

(54) ***MAGNOLIA* TREE NAMED 'NCMX1'**

(50) Latin Name: ***Magnolia* sp.**
Varietal Denomination: NCMX1

(71) Applicant: North Carolina State University, Raleigh, NC (US)

(72) Inventor: Thomas G. Ranney, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 58 days.

(21) Appl. No.: 14/999,119

(22) Filed: Mar. 31, 2016

(65) Prior Publication Data

US 2017/0290221 P1 Oct. 5, 2017

(51) Int. Cl.
*A01H 5/00* (2018.01)
*A01H 5/02* (2018.01)

(52) U.S. Cl.
USPC ..... Plt./223
CPC ..... *A01H 5/02* (2013.01)

(58) Field of Classification Search
USPC ..... Plt./216, 223
See application file for complete search history.

(56) References Cited

PUBLICATIONS

Parris et al. "Ploidy Levels, Relative Genome Sizes, and Base Pair Composition in *Magnolia*", *J. Amer. Soc. Hort. Sci.* 135(6):533-547, 2010.

J. Frank Schmidt & Son Co., Mercury *Magnolia*, posted Jun. 24, 2015 http://jfschmidt.com/pdfs/mercurymagnolia.pdf.

North Carolina State University, Mountain Crop Improvement Lab, Mercury *Magnolia*, posted Sep. 9, 2015, https://www.ces.ncsu.edu/fletcher/mcilab/introductions/mercury-magnolia.html.

Plantkeuze, Get Inspired, *Magnolia* Mercury 'NCMX1', posted Jan. 1, 2016; https://www.facebook.com (Posting no longer available).

*Primary Examiner* — Susan McCormick Ewoldt
*Assistant Examiner* — Karen M Redden
(74) *Attorney, Agent, or Firm* — Myers Bigel, P.A.

(57) ABSTRACT

'NCMX1' is a new cultivar of *magnolia* with large, fragrant red-purple flowers, an upright habit and a late flowering time.

4 Drawing Sheets

Latin name of the genus and species: The Latin name of the novel plant variety disclosed herein is *Magnolia* sp.

Variety denomination: The inventive hybrid of (*Magnolia×loebneri* 'Encore')×(*Magnolia×soulangeana* 'Alexandrina') disclosed herein has been given the varietal denomination 'NCMX1'.

BACKGROUND OF THE INVENTION

The present invention comprises a new and distinct hybrid *magnolia* cultivar hereinafter referred to by the cultivar name 'NCMX1'. This new *magnolia* was developed through a breeding program located in Mills River, N.C. 'NCMX1' was selected from a population of seedlings grown from a controlled cross of *Magnolia×loebneri* 'Encore' (unpatented, female parent)×*Magnolia×soulangeana* 'Alexandrina' (unpatented, male parent). The first asexual propagation of 'NCMX1' was carried out in July 2005 by budding onto *Magnolia acuminata* root stock in Mills River, N.C. and has been asexually reproduced repeatedly by budding over a 10-year period. 'NCMX1' has been found to retain its distinctive characteristics through successive asexual propagations.

SUMMARY OF THE INVENTION

The following are the unique combination of characteristics of this new cultivar when grown under standard horticultural practices in Mills River, N.C.

1. Red/purple flower buds prior to opening (outer tepals).

2. Large (25-30 cm in diameter) fragrant flowers having light lavender/pink inner tepals and red/purple outer tepals.
3. Upright habit with distinct central leader and excurrent form.
4. Particularly late flowering time (late April-early May in Mills River, N.C.) for plants with similar parentage.

BRIEF DESCRIPTION OF THE DRAWINGS

This new *magnolia* is illustrated by the accompanying photographs which show the plant's form, foliage and flowers. The colors shown are as true as can be reasonably obtained by conventional photographic procedures. Colors in the photographs may differ slightly from the color values cited in the detailed botanical description, which accurately describe the colors of the new hybrid *magnolia*.

DETAILED BOTANICAL DESCRIPTION

Figure 1:
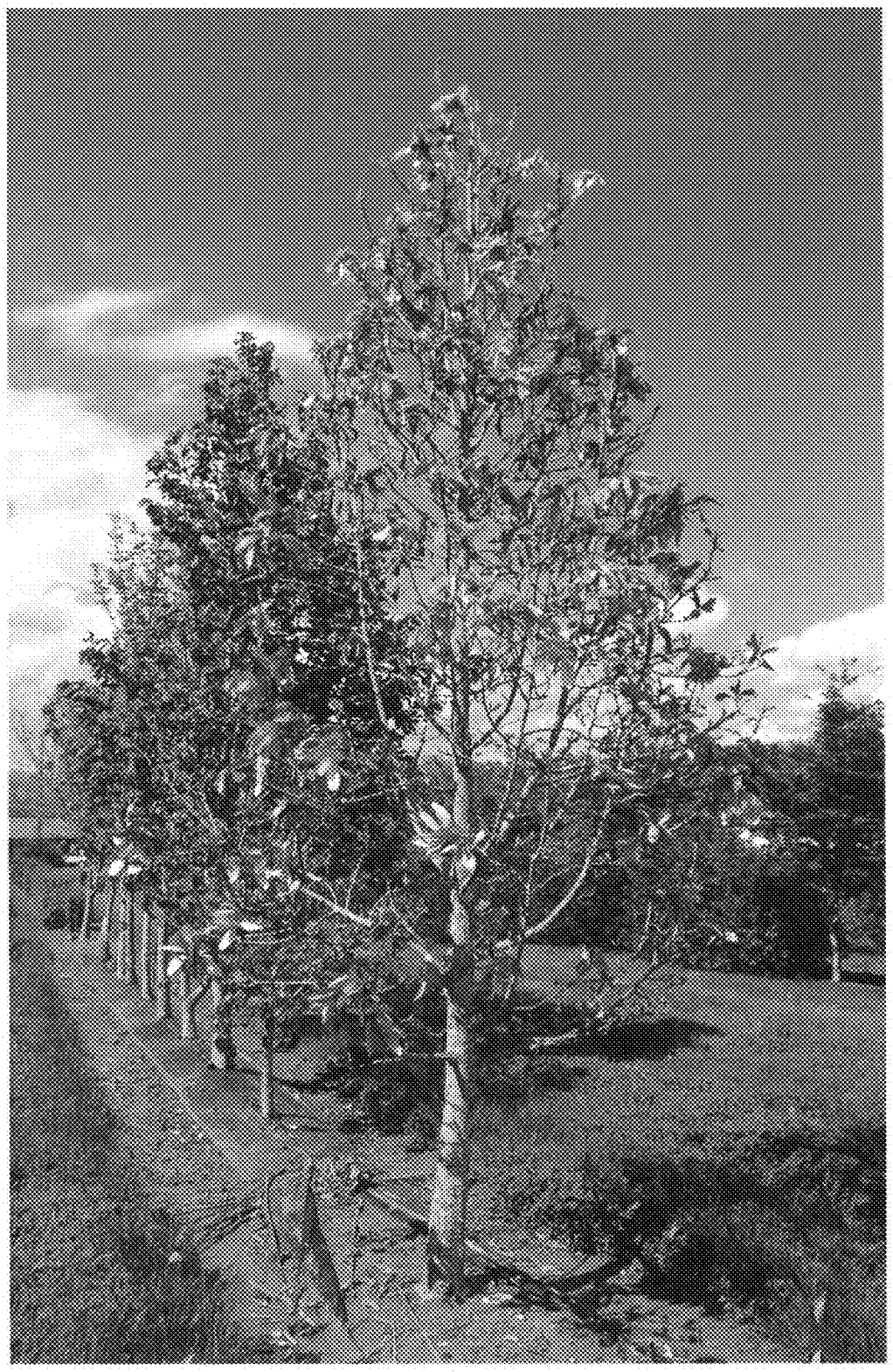
FIG. 1 is a photograph showing the overall tree form and flowers of 'NCMX1' taken on Apr. 29, 2013 of a 12-year-old tree.
Figure 2:
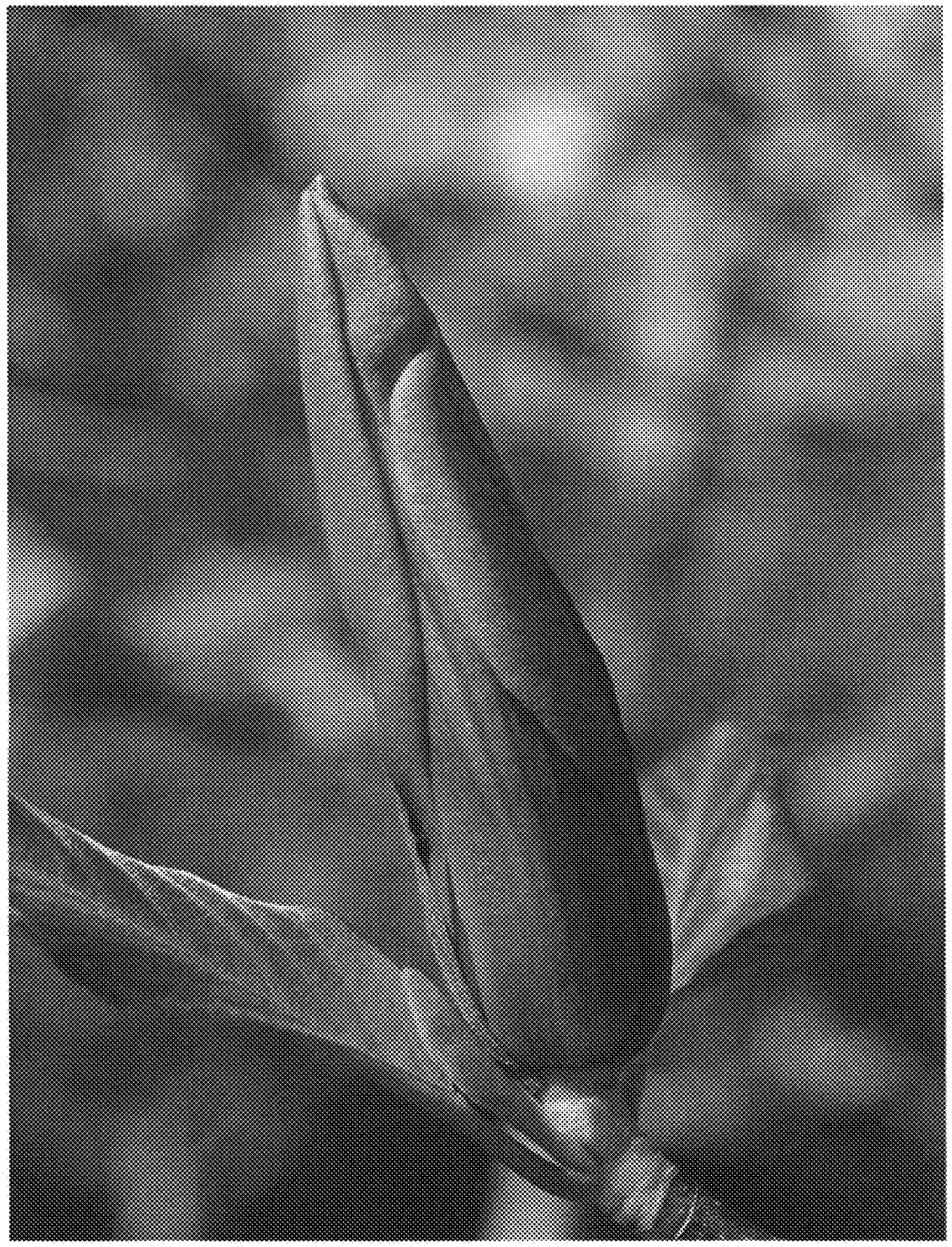
FIG. 2 is a photograph showing a developing flower bud from a 7-year-old tree of 'NCMX1', prior to opening, taken on May 5, 2008.
Figure 3:
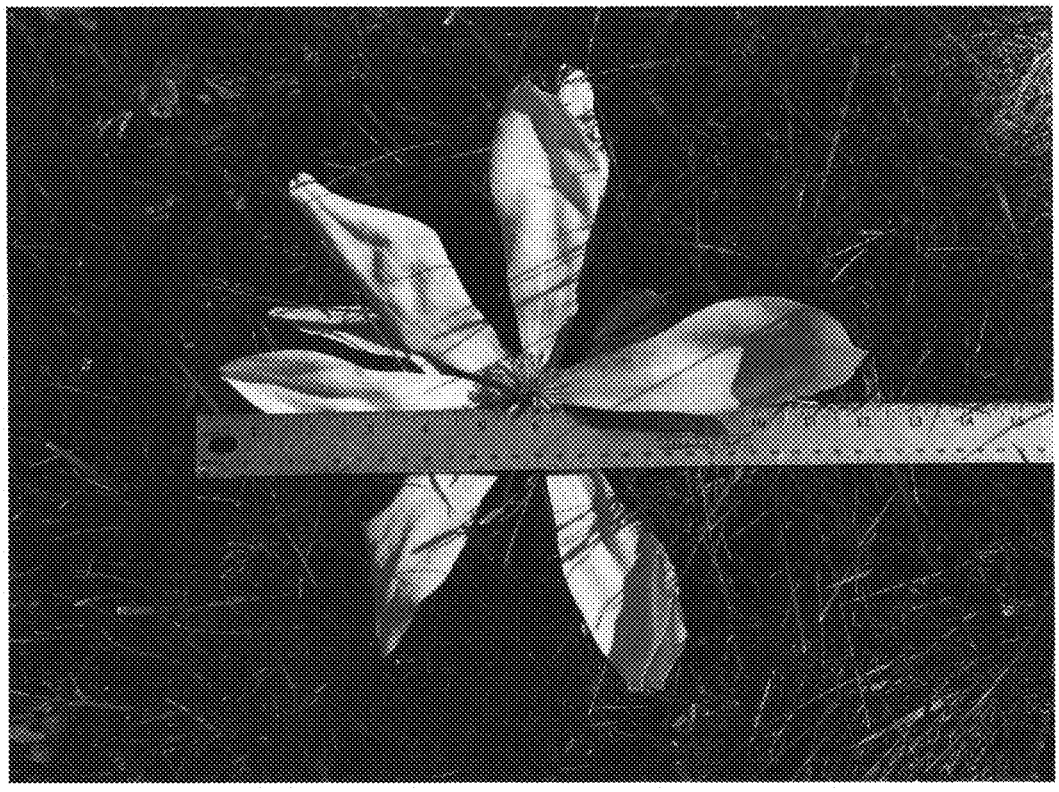
FIG. 3 is a photograph showing the dimensions of an open flower from a 12-year-old of 'NCMX1' taken on Apr. 30, 2013.
Figure 4:
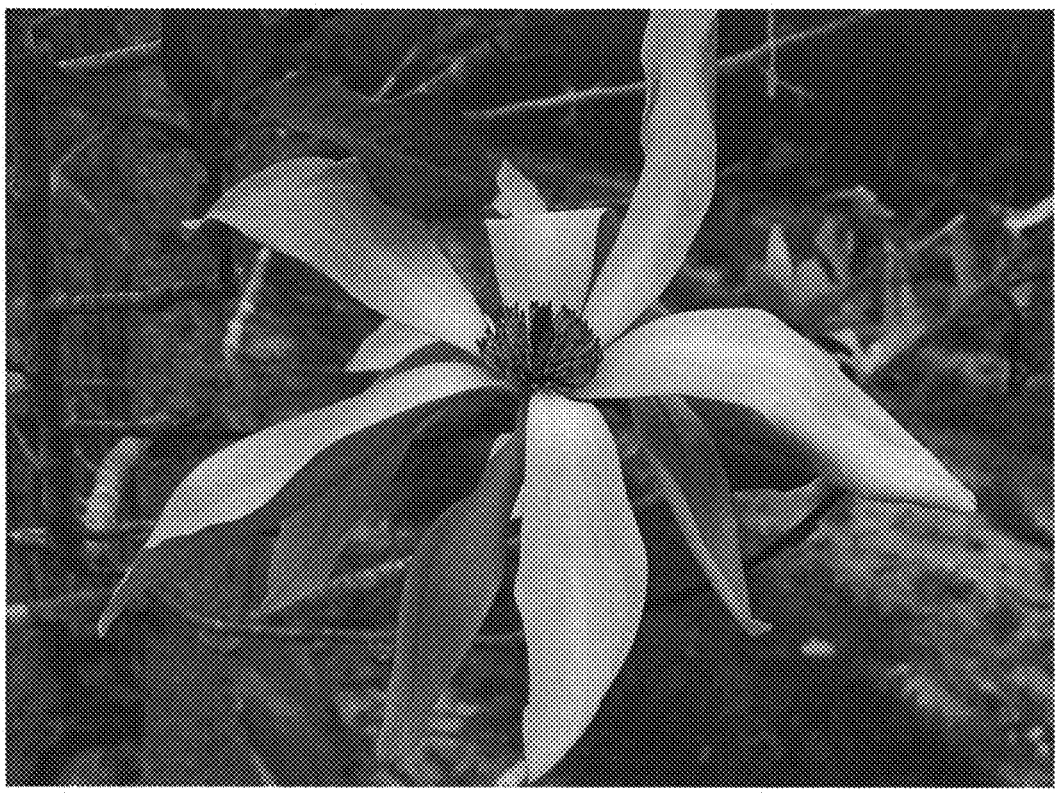
FIG. 4 is a photograph showing the form and color of an open flower from a 10-year-old tree of 'NCMX1' taken on Apr. 15, 2011.

The following is a detailed description of the botanical characteristics of the new and distinct hybrid *magnolia* variety plant known by the denomination 'NCMX1'. The detailed description was taken on a ten-year-old field-grown plant in Mills River, N.C. in 2013. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Magnolia* sp. 'NCMX1'.

*Common name.*—*Magnolia.*

Parentage: [*Magnolia×loebneri* 'Encore' (unpatented)]× [*Magnolia×soulangeana* 'Alexandrina' (unpatented)].

Plant description:

*Growth habit.*—Upright branching habit with an obovate crown and excurrent form.

*Height.*—Approximately 8 m.

*Width.*—Approximately 3-4 m.

Current year shoots:

*Shoot diameter.*—Avg. 0.7 cm (range: 0.5 to 4 cm).

*Shoot length.*—Avg. 100 cm (range: 75 to 200 cm).

*Internode length.*—Avg. 6 cm (range: 3 to 8.5 cm).

*Shoot color.*—Immature: Yellow-green (146A). Mature: Brown (N200A).

*Shoot texture.*—Pubescence on immature branches. Mature branches glabrous.

*Lenticels.*—Approximately 0.1 cm in diameter, greyed-white (156C).

Leaves:

*Type.*—Single.

*Persistence.*—Deciduous.

*Arrangement.*—Alternate.

*Shape.*—Ovate.

*Apex.*—Acute to acuminate.

*Base.*—Cuneate.

*Venation.*—Reticulate.

*Vein color.*—Upper: Yellow-green (146C). Lower: Yellow-green (145C).

*Margins.*—Entire, undulate.

*Emerging leaves.*—Color: Upper: Green (139A). Lower: Greyed-green (189A). Texture: Pubescent.

*Mature leaves during growing season.*—Color: Upper: Green (139A). Lower: Greyed-green (189A). Texture: Pubescent. Length of lamina: Avg. 15.9 cm (13.0 to 19.3 cm). Width: Avg. 10.4 cm (8.7 to 13.5 cm).

*Autumn foliage color.*—Moderate Yellow Green (146B) to Moderate Brown (165A).

*Leaf attachment.*—Petiolate.

*Petiole.*—Length: Avg. 2.1 cm (1.2 to 4 cm). Diameter: Avg. 0.24 cm (0.15 to 0.35 cm). Color: Yellow-green (146C). Texture: Puberulent.

Inflorescence:

*Description.*—Individual, complete flowers.

*Flowering season.*—Late April to early May in Mills River, N.C.

*Flowering duration.*—3-4 weeks.

*Duration of each flower.*—5 to 7 days.

*Fragrance.*—Yes.

*Bud.*—Shape: Conical, initially opening to an urn shape. Length: 10 cm. Diameter: 2.5 cm. Color: Red-Purple (59A-59C).

*Flower aspect.*—Upright.

*Flower shape.*—Open urn-shaped with arching tepals as flower ages.

*Flower diameter.*—25 to 31 cm.

*Flower height.*—About 10 cm.

*Tepals.*—Arrangement: Whorled. Number: Typically 9. Fused or not fused: Not fused. Texture: Glabrous, lustrous. Shape: Oblanceolate. Margin: Entire. Apex: Obtuse. Length: 12 to 15 cm. Width: 4.5 to 5 cm. Color when fully opened: Upper: Light lavender (75C) with speckling of pink (64D). Lower: Ranging from Red-Purple (60B) to Red-Purple (60D). Flower color upon opening Upper: Light lavender (75B) with speckling of pink (64D). Lower: Ranging from Red-Purple (60A) to Red-Purple (60D).

*Peduncle.*—Length: 1 cm. Diameter: 0.5 to 0.7 cm. Color: Green (143C).

Reproductive organs:

*Gynandrophore.*—Length: 1.5 to 2.2 cm. Width: 0.5 to 0.7 cm.

*Gynoecium.*—Follicle number: 25-35. Color: Red-Purple (59A-59C).

*Androecium.*—Stamen number: Approximately 80. Anther length: 1.8 to 2.2 cm. Anther width: 0.5 to 0.7 cm. Anther color: Greyed-Yellow (161D) with Red-Purple (60A) stripes on outer and inner surfaces.

Trunk:

*Diameter.*—20 cm (at 30 cm above the soil line).

*Texture.*—Scaly.

*Color.*—Light brownish grey (N200C).

*Lenticels.*—0.25-0.5 cm long; Light brownish grey (N200C).

Branches:

*Color.*—Light brownish grey (N200C).

*Average length.*—Varies from 2 to 4 M.

*Average diameter.*—7-10 cm at intersection with trunk.

Fruit and seed: None produced to date.

Disease and insect resistance: No significant disease or insect pests have been observed.

Cold hardiness: At least USDA zone 6b; testing has not been completed in colder zones.

COMPARISON WITH COMMERCIAL CULTIVARS AND PARENTS

'NCMX1' is distinguished from the commercial cultivar *Magnolia* 'Galaxy' (unpatented) in that 'NCMX1' has larger flowers, a more narrow habit, and more fragrant flowers. 'NCMX1' has flowers that are 25 to 31 cm in diameter and a mature tree width of 3-4 m whereas 'Galaxy' has flowers that are 20 to 25 cm in diameter and a mature tree width of 6-8 m. 'NCMX1' is distinguished from its parent *Magnolia× loebneri* 'Encore' in that 'NCMX1' has red-purple flowers with 9 tepals while 'Encore' has white flowers with 18-25 tepals. 'NCMX1' is distinguished from its parent *Magnolia× soulangeana* 'Alexandrina' in that 'NCMX1' has larger tepals (12-15 cm long) that are light lavender with some pink on the inner/upper surface while 'Alexandrina' has smaller tepals (10 cm long) that are white on the inner/upper surface.

What is claimed is:

1. A new and distinct hybrid *magnolia* plant named 'NCMX1' substantially as illustrated and described herein.

* * * * *